United States Patent
Erramilli et al.

(10) Patent No.: US 12,119,105 B2
(45) Date of Patent: Oct. 15, 2024

(54) ENGAGEMENT MONITORING ENGINE FOR PHARMACEUTICAL ARTICLES

(71) Applicant: ACTO Technologies Inc., Toronto (CA)

(72) Inventors: Kumar Karthik Erramilli, Pickering (CA); Parth Khanna, Toronto (CA); Kapil Kalra, Mississauga (CA)

(73) Assignee: ACTO Technologies Inc., Toronto (CA)

( * ) Notice: Subject to any disclaimer, the term of this patent is extended or adjusted under 35 U.S.C. 154(b) by 242 days.

(21) Appl. No.: 17/170,083

(22) Filed: Feb. 8, 2021

(65) Prior Publication Data
US 2022/0254478 A1    Aug. 11, 2022

(51) Int. Cl.
| | | |
|---|---|---|
| G16H 40/20 | (2018.01) | |
| G06N 5/04 | (2023.01) | |
| G09B 7/00 | (2006.01) | |
| G16H 50/00 | (2018.01) | |
| G16H 50/70 | (2018.01) | |

(Continued)

(52) U.S. Cl.
CPC ............. *G16H 40/20* (2018.01); *G06N 5/04* (2013.01); *G09B 7/00* (2013.01); *G16H 50/70* (2018.01); *G16H 70/40* (2018.01); *H04L 67/12* (2013.01)

(58) Field of Classification Search
CPC ................................................ G06Q 50/20–26
See application file for complete search history.

(56) References Cited

U.S. PATENT DOCUMENTS 10,496,719 B2 * 12/2019 Khanna ............... G06F 16/9535
11,301,527 B2 *  4/2022 Khanna ................. H04L 67/535
(Continued)

FOREIGN PATENT DOCUMENTS

WO     WO-2007089686 A2 *  8/2007     ........... G06F 19/321

OTHER PUBLICATIONS

Q. Zhang, G. Zhang, J. Lu and D. Wu, "A Framework of Hybrid Recommender System for Personalized Clinical Prescription," 2015 10th International Conference on Intelligent Systems and Knowledge Engineering (ISKE), Taipei, Taiwan, 2015, pp. 189-195, doi: 10.1109/ISKE.2015.98. (Year: 2015).*

(Continued)

*Primary Examiner* — Christopher L Gilligan
*Assistant Examiner* — Jessica Marie Webb
(74) *Attorney, Agent, or Firm* — Fernando & Partners, LLP

(57) ABSTRACT

Various implementations disclosed herein include devices, systems, and methods for monitoring engagement associated with pharmaceutical articles. In various implementations, a device includes a non-transitory memory and a processor coupled with the non-transitory memory. In some implementations, a method includes obtaining engagement data indicating engagement associated with a pharmaceutical article. In some implementations, the method includes identifying a plurality of topics associated with the pharmaceutical article. In some implementations, the method includes determining respective comprehension scores for the plurality of topics based on the engagement data. In some implementations, the method includes recommending a set of one or more media content items related to a subset of the plurality of topics based on the respective comprehension scores for the plurality of topics.

22 Claims, 9 Drawing Sheets

(51) Int. Cl.
*G16H 70/40* (2018.01)
*H04L 67/12* (2022.01)

(56) References Cited

U.S. PATENT DOCUMENTS

| | | | | |
|---|---|---|---|---|
| 11,487,833 | B2* | 11/2022 | Khanna | G06F 16/9535 |
| 11,676,603 | B2* | 6/2023 | Erramilli | G06F 40/30 |
| | | | | 704/270.1 |
| 2002/0187463 | A1* | 12/2002 | Aspe | G16H 10/60 |
| | | | | 434/362 |
| 2005/0194744 | A1* | 9/2005 | Robbins | A63F 9/183 |
| | | | | 273/430 |
| 2013/0262196 | A1* | 10/2013 | Scalici | G16H 70/40 |
| | | | | 705/14.1 |
| 2017/0178525 | A1* | 6/2017 | Kwan | H04L 67/02 |
| 2018/0174684 | A1* | 6/2018 | Eastman | G16H 50/20 |
| 2020/0111044 | A1* | 4/2020 | New, Jr. | G06Q 10/063112 |
| 2020/0356613 | A1* | 11/2020 | Khanna | H04L 67/535 |
| 2020/0379986 | A1* | 12/2020 | Erramilli | G06F 16/90332 |
| 2021/0005099 | A1* | 1/2021 | Agley | G06N 7/01 |

OTHER PUBLICATIONS (N.a.), "Youtube_Joking_Bad", 2015, Youtube, Accessed via Internet Archive, all pages. (Year: 2015).*

* cited by examiner

ENGAGEMENT MONITORING ENGINE FOR PHARMACEUTICAL ARTICLES

TECHNICAL FIELD

The present disclosure generally relates to monitoring engagement associated with a pharmaceutical article.

BACKGROUND

Some content generation entities generate media content items that provide information regarding a physical article. For example, a manufacturer of a pharmaceutical article may generate media content items that provide information regarding the pharmaceutical article.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1A:
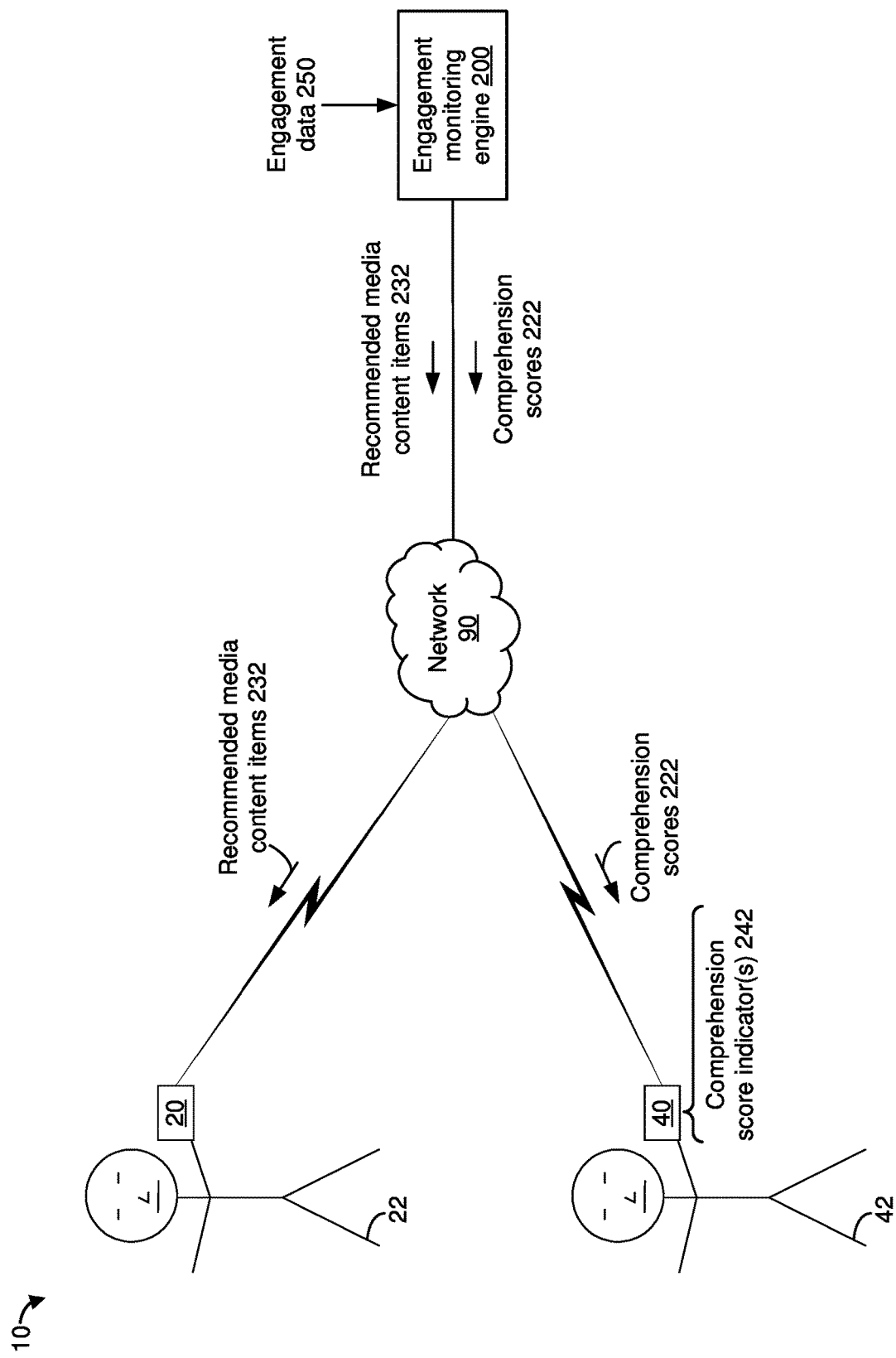
FIG. 1A is a diagram of an example operating environment in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for monitoring engagement associated with pharmaceutical articles. In various implementations, a device includes a non-transitory memory and a processor coupled with the non-transitory memory. In some implementations, a method includes obtaining engagement data indicating engagement associated with a pharmaceutical article. In some implementations, the method includes identifying a plurality of topics associated with the pharmaceutical article. In some implementations, the method includes determining respective comprehension scores for the plurality of topics based on the engagement data. In some implementations, the method includes recommending a set of one or more media content items related to a subset of the plurality of topics based on the respective comprehension scores for the plurality of topics.

In accordance with some implementations, a device includes one or more processors, a non-transitory memory, and one or more programs. In some implementations, the one or more programs are stored in the non-transitory memory and are executed by the one or more processors. In some implementations, the one or more programs include instructions for performing or causing performance of any of the methods described herein. In accordance with some implementations, a non-transitory computer readable storage medium has stored therein instructions that, when executed by one or more processors of a device, cause the device to perform or cause performance of any of the methods described herein. In accordance with some implementations, a device includes one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

Some content generation entities generate media content items that provide information regarding a physical article. For example, a manufacturer of a pharmaceutical article may generate media content items that provide information regarding the pharmaceutical article. A physical article may be associated with various topics, and a content generation entity may distribute media content items that provide information regarding the various topics in order to inform users about the physical article. However, a user may understand some topics more than others. As such, there may be a need to provide the user with more media content items that relate to topics that the user does not understand and fewer media content items that relate to topics that the user understands.

The present disclosure provides methods, systems and/or devices for monitoring engagement associated with a physical article such as a pharmaceutical article (e.g., a pharmaceutical drug or a medical device). A device utilizes engagement data indicating engagement associated with a physical article to determine comprehension scores for topics related to the physical article and recommend media content items for topics with comprehension scores that are below a threshold score (e.g., for topics with relatively low comprehension scores).

A device determines respective comprehension scores for topics that relate to a physical article. The comprehension scores indicate how well a user understands corresponding topics. The device uses the comprehension scores to recommend media content items to a user. The device can recommend media content items that provide information regarding topics that the user does not comprehend as well as desired. For example, the device can recommend media content items for topics with comprehension scores that are below a threshold score. The device can forgo recommending media content items that provide information regarding topics that the user comprehends as well as desired. For example, the device can forgo recommending media content items for topics with comprehension scores that are greater than the threshold score.

The device can determine the comprehension scores based on engagement data associated with the physical article. Engagement data associated with the physical article can indicate engagement with media content items that provide information regarding the physical article. For example, the engagement data can indicate whether or not a user has viewed a media content item that provides information regarding a physical article. As another example, the engagement data can include a quiz score on a quiz related to the physical article. Engagement data associated with the physical article can indicate a number of transactions relation to the physical article. For example, the engagement data can indicate a quantity of the physical article that the manufacturer has transported to consumers. Engagement data associated with the physical article can indicate a number of times that the physical article has been recommended by a set of authorized recommenders. For example, the engagement data for a pharmaceutical article can indicate a number of times that the pharmaceutical article has been prescribed by healthcare providers.

Determining respective comprehension scores for the topics provides a more granular view of how well a user of the device understands individual topics related to the physical article, for example, as opposed to how well the user understands the physical article as a whole. Obtaining a more granular view of how well the user understands the individual topics allows the device to recommend and/or present media content items that may help the user in increasing the user's understanding of the individual topics and consequently increase engagement with the physical article.

Recommending media content items based on the comprehension scores enhances discoverability of content by allowing the device to recommend media content items that a user may not otherwise discover. For example, if the user uses a name of the physical article as a search term, a search engine may not present a media content item related to a topic that the user does not understand well because the media content item may not be mapped to the name of the physical article in an index of the search engine.

Recommending media content items based on the comprehension scores tends to enhance operability of the device by reducing a need for a user to manually search for media content items that provide information regarding topics that the user does not understand as well as desired. For example, the user need not specifically search for media content items that are related to a topic that the user does not understand well.

Recommending media content items based on comprehension scores tends to trigger an increase in the comprehension scores over a period of time. For example, as the user reviews the media content items, the user's comprehension of the topics that the media content items relate to will likely increase. Recommending media content items for topics that the user does not understand as well as desired tends to increase an overall understanding of the physical article by the user. For example, as the user's understanding of certain topics associated with the physical article increases, the user's overall understanding of the physical article may also increase. As the user's understanding of the various topics associated with the physical article increases, the engagement associated with the physical article may also increase. For example, as a medical representative understands more about a pharmaceutical drug, the medical representative may be able to convince more clinicians to prescribe the pharmaceutical drug thereby increasing a number of prescriptions generated for the pharmaceutical drug.

FIG. 1A is a diagram of an example operating environment 10 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 10 includes a user device 20 operable by a user 22, an administrator device 40 operable by an administrator 42, an engagement monitoring engine 200, and a network 90 (e.g., a private network or a public network such as a portion of the Internet). Examples of the user device 20 and the administrator device 40 include a mobile computing device (e.g., a smartphone, a tablet, a laptop computer, or a wearable computing device such as an electronic watch or a head-mountable device), a desktop computer and/or a television. Although the engagement monitoring engine 200 is shown as being separate from the user device 20 and the administrator device 40, in some implementations, at least a portion of the engagement monitoring engine 200 resides at the user device 20 and/or the administration device 40. In some implementations, the engagement monitoring engine 200 resides at a server computer. In some implementations, the engagement monitoring engine 200 is implemented by a cloud computing platform. In some implementations, the user 22 is a medical representative that represents a pharmaceutical article (e.g., a pharmaceutical drug or a medical device), and the user device 20 is referred to as a medical representative device. In some implementations, the user 22 is a patient, and the user device 20 is referred to as a patient device. In some implementations, the user 22 is a healthcare provider, and the user device 20 is referred to as a healthcare provider device. In some implementations, the administrator 42 represents a manufacturer of a pharmaceutical device, and the administrator device 40 is referred to as a pharmaceutical manufacturer device.

In various implementations, the engagement monitoring engine 200 obtains engagement data 250 that indicates engagement associated with an article (e.g., a physical article, for example, a pharmaceutical article such as a pharmaceutical drug or a medical device). In some implementations, the engagement monitoring engine 200 obtains at least a portion of the engagement data 250 from the user device 20. In some implementations, the engagement monitoring engine 200 obtains at least a portion of the engagement data 250 from the administrator device 40. In some implementations, the engagement monitoring engine 200 obtains at least a portion of the engagement data 250 from a remote data source (e.g., from the content distribution platform 260, the CRM system 270 and/or the healthcare management system 280 shown in FIG. 2).

In some implementations, the engagement data 250 indicates engagement of the user device 20 and/or the user 22 with content related to the article. For example, in some implementations, the engagement data 250 indicates whether or not the user device 20 has accessed a media content item that provides information regarding a pharmaceutical drug or a medical device. In some implementations, the engagement data 250 includes an engagement score that indicates a quality of the engagement of the user device 20 and/or the user 22 with content related to the article. For example, in some implementations, the engagement data 250 includes a quiz score on a quiz related to a topic that the administrator device 40 has associated with a pharmaceutical drug or a medical device.

In some implementations, the engagement monitoring engine 200 utilizes the engagement data 250 to generate a set of one or more comprehension scores 222 ("comprehension scores 222", hereinafter for the sake of brevity) that indicate comprehension of a set of one or more topics associated with the physical article by the user 22. For example, in some implementations, the comprehension scores 222 indicate how well the user 22 understands the topics associated with the physical article that the engagement monitoring engine 200 is monitoring. In some implementations, the engagement monitoring engine 200 provides the comprehension scores 222 to the administrator device 40, and the administrator device 40 displays comprehension score indicators 242 indicating the comprehension scores 222.

In some implementations, the engagement monitoring engine 200 includes a recommendation engine (e.g., the content recommender 230 shown in FIG. 2) that recommends a set of one or more media content items 232 ("recommended media content items 232", hereinafter for the sake of brevity) to the user device 20 based on the engagement data 250. In some implementations, the engagement monitoring engine 200 identifies the recommended media content items 232 based on the comprehension scores 222. For example, if a physical article is associated with a set of topics, the recommended media content items 232 may include a media content item that provides information regarding a subset of the set of topics with comprehension scores 222 that are lower than a threshold comprehension score. In this example, the engagement monitoring engine 200 recommends a media content item related to a topic with a low comprehension score 222 in order to increase a likelihood of increasing the comprehension score 222 beyond the threshold comprehension score (e.g., in order to increase an understanding of the user 22 of the topic with the low comprehension score 222).

Figure 1B:
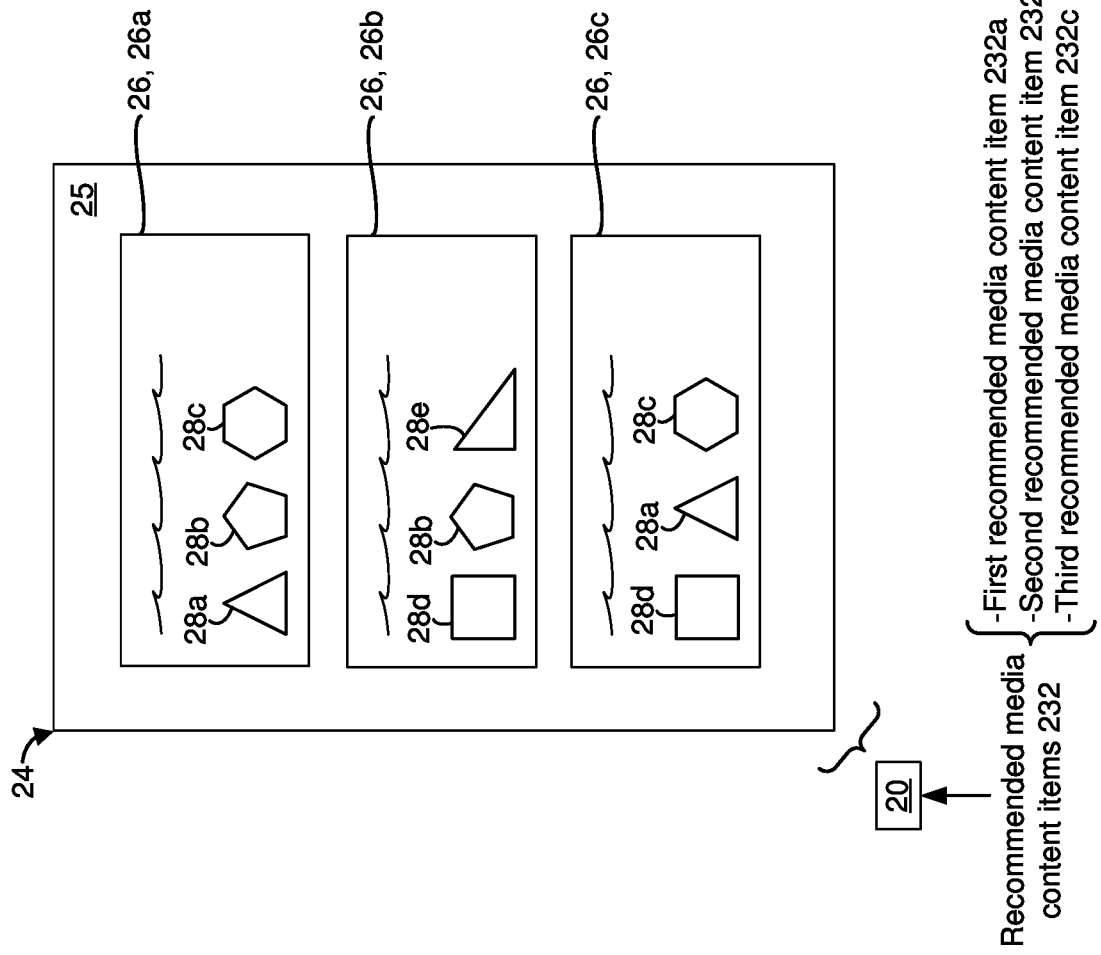
FIGS. 1B-1F are diagrams of example user interfaces in accordance with some implementations.

FIG. 1B illustrates an example graphical user interface (GUI) 25 that the user device 20 displays on a display 24 of the user device 20. As shown in FIG. 1B, the GUI 25 includes representations 26 of the recommended media content items 232. In the example of FIG. 1B, the representations 26 include a first representation 26a of a first recommended media content item 232a, a second representation 26b of a second recommended media content items 232b, and a third representation 26c of a third recommended media content item 232c. In some implementations, the representations 26 indicate respective titles of the recommended media content items 232.

In some implementations, the representations 26 indicate respective topics of the recommended media content items 232. In the example of FIG. 1B, the first representation 26a includes a first symbol 28a (e.g., a triangle) representing a first topic, a second symbol 28b (e.g., a pentagon) representing a second topic, and a third symbol 28c (e.g., an octagon) representing a third topic. Displaying the first symbol 28a, the second symbol 28b and the third symbol 28c within the first representation 26a indicates that the first recommended media content item 232a provides information regarding the first topic, the second topic and the third topic.

In the example of FIG. 1B, the second representation 26b includes a fourth symbol 28d (e.g., a square) representing a fourth topic, the second symbol 28b representing the second topic, and a fifth symbol 28e (e.g., a right triangle) representing a fifth topic. Displaying the fourth symbol 28d, the second symbol 28b and the fifth symbol 28e within the second representation 26b indicates that the second recommended media content item 232b provides information regarding the fourth topic, the second topic and the fifth topic.

In the example of FIG. 1B, the third representation 26c includes the fourth symbol 28d representing the fourth topic, the first symbol 28a representing the first topic, and the third symbol 28c representing the third topic. Displaying the fourth symbol 28d, the first symbol 28a and the third symbol 28c within the third representation 26c indicates that the third recommended media content item 232c provides information regarding the fourth topic, the first topic and the third topic.

Figure 1C:
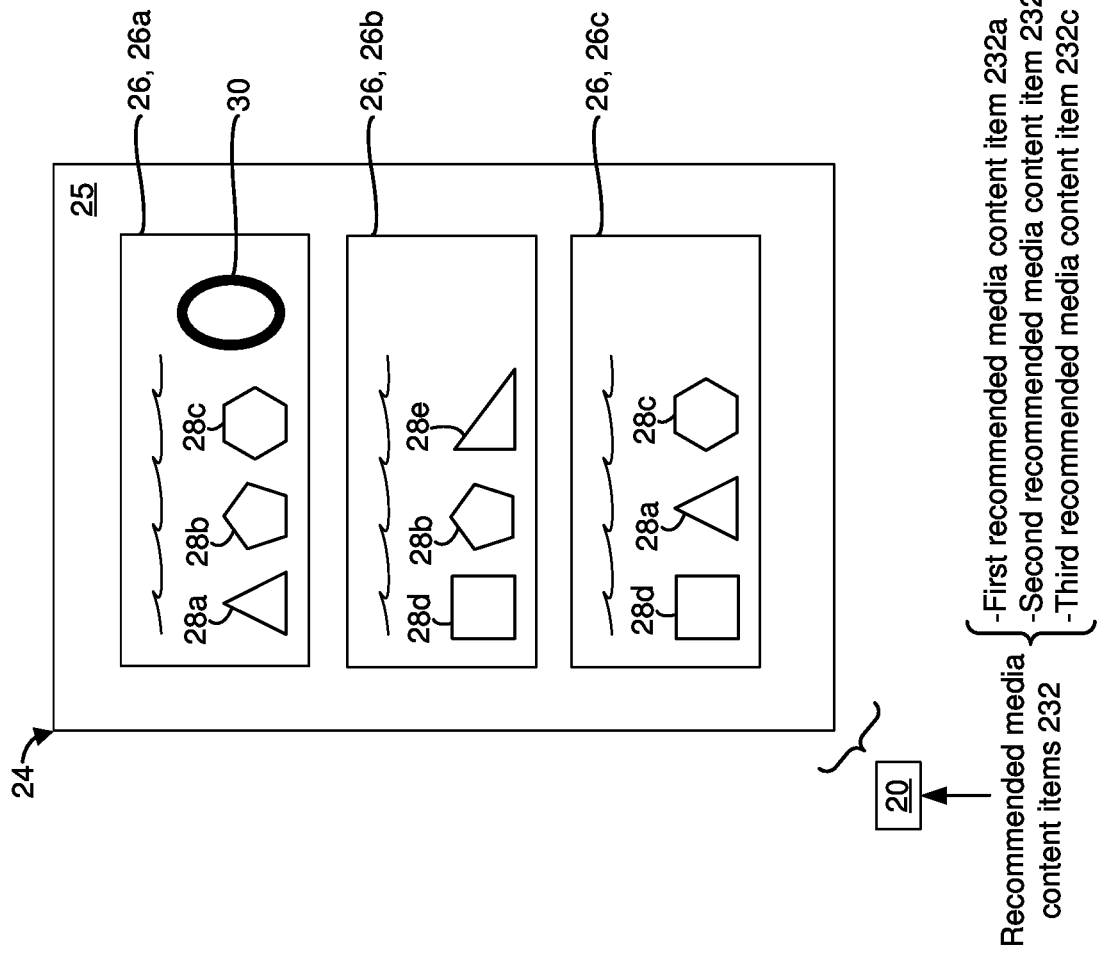

FIG. 1C illustrates a user input 30 directed to the first representation 26a of the first recommended media content item 232a. In some implementations, the user input 30 includes a tap gesture (e.g., a single contact at a location corresponding to the first representation 26a). In some implementations, the user input 30 corresponds to a request to view the first recommended media content item 232a.

Figure 1D:
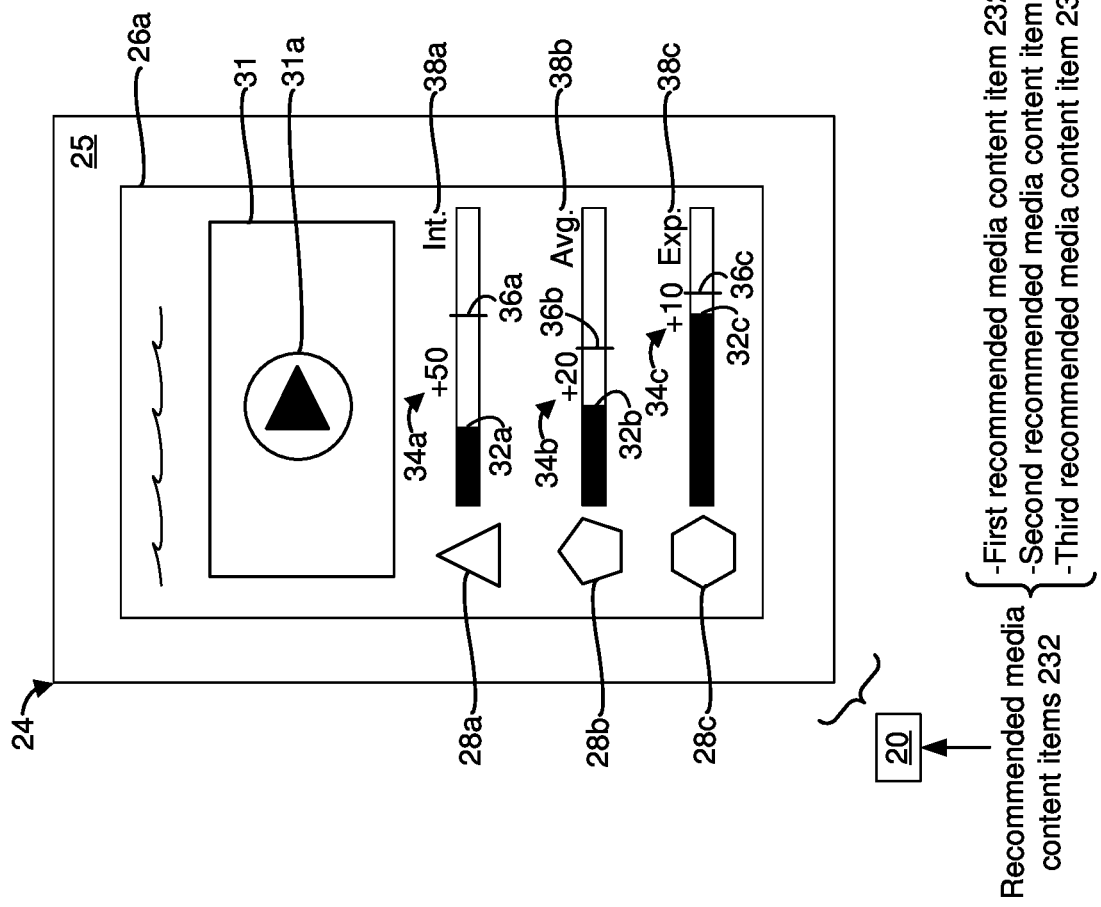

FIG. 1D illustrates an expanded view of the first representation 26a of the first recommended media content item 232a. As shown in FIG. 1D, in some implementations, the first recommended media content item 232a includes a video 31 that the user 22 of the user device 20 can view by activating a play affordance 31a. In some implementations, the first recommended media content item 232a includes text or a graphic (e.g., an image, a chart, etc.).

As indicated by the first symbol 28a, the first recommended media content item 232a provides information regarding the first topic. In some implementations, the expanded view of the first representation 26a indicates a first current comprehension score 32a of the user 22 in the first topic. In some implementations, the first current comprehension score 32a indicates how well the user 22 understands the first topic. In some implementations, the first current comprehension score 32a is a function of (e.g., based on) a quiz score in a quiz that relates to the first topic. More generally, in various implementations, the first current comprehension score 32a is a function of the engagement data 250. Similarly, the expanded view of the first representation 26a indicates a second current comprehension score 32b of the user 22 in the second topic and a third current comprehension score 32c of the user 22 in the third topic.

In some implementations, the expanded view of the first representation 26a indicates a first expected increase 34a in the first current comprehension score 32a upon reviewing the first recommended media content item 232a in its entirety. In the example of FIG. 1D, the first expected increase 34a has a numerical value of 50 points. Similarly, in some implementations, the expanded view of the first representation 26a indicates a second expected increase 34b in the second current comprehension score 32b upon reviewing the first recommended media content item 232a in its entirety. In the example of FIG. 1D, the second expected increase 34b has a numerical value of 20 points. In some implementations, the expanded view of the first representation 26a indicates a third expected increase 34c in the third current comprehension score 32c upon reviewing the first recommended media content item 232a in its entirety. In the example of FIG. 1D, the third expected increase 34c has a numerical value of 10 points. In various implementations, the first expected increase 34a, the second expected increase 34b and the third expected increase 34c include respective numerical values by which the corresponding comprehension scores 32a, 32b and 32c are expected to increase upon reviewing the first recommended media content item 232a in its entirety.

In some implementations, the expanded view of the first representation 26a indicates a first target comprehension score 36a for the user 22 in the first topic. In some implementations, the first target comprehension score 36a is a score that the user 22 is expected to have upon completion of the first recommended media content item 232a. In some implementations, the first target comprehension score 36a is a function of the first current comprehension score 32a and the first expected increase 34a. For example, in some implementations, the first target comprehension score 36a is a sum of the first current comprehension score 32a and the first expected increase 34a. As shown in FIG. 1D, in some implementations, the expanded view of the first representation 26a indicates a second target comprehension score 36b for the user 22 in the second topic, and a third target comprehension score 36c for the user 22 in the third topic. Similar to the first target comprehension score 36a, in some implementations, the second target comprehension score 36b is a function of (e.g., a sum of) the second current comprehension score 32b and the second expected increase 34b. Similar to the first target comprehension score 36a and the second target comprehension score 36b, in some implementations, the third target comprehension score 36c is a function of (e.g., a sum of) the third current comprehension score 32c and the third expected increase 34c.

In some implementations, the expanded view of the first representation 26a indicates respective comprehension levels of the user 22 in the first topic, the second topic and the third topic. For example, as shown in FIG. 1D, the first representation 26a indicates a first comprehension level 38a of the user 22 in the first topic, a second comprehension level 38b of the user 22 in the second topic, and a third comprehension level 38c of the user 22 in the third topic. In some implementations, the comprehension levels 38a, 38b and 38c are a function of (e.g., based on) the current comprehension scores 32a, 32b and 32c, respectively. In the example of FIG. 1D, the user 22 has an intermediate comprehension level in the first topic, an average comprehension level in the second topic, and an expert comprehension level in the third topic. In various implementations, the administrator device 40 defines the comprehension levels and a mapping of the comprehension levels to the comprehension scores.

Figure 1E:
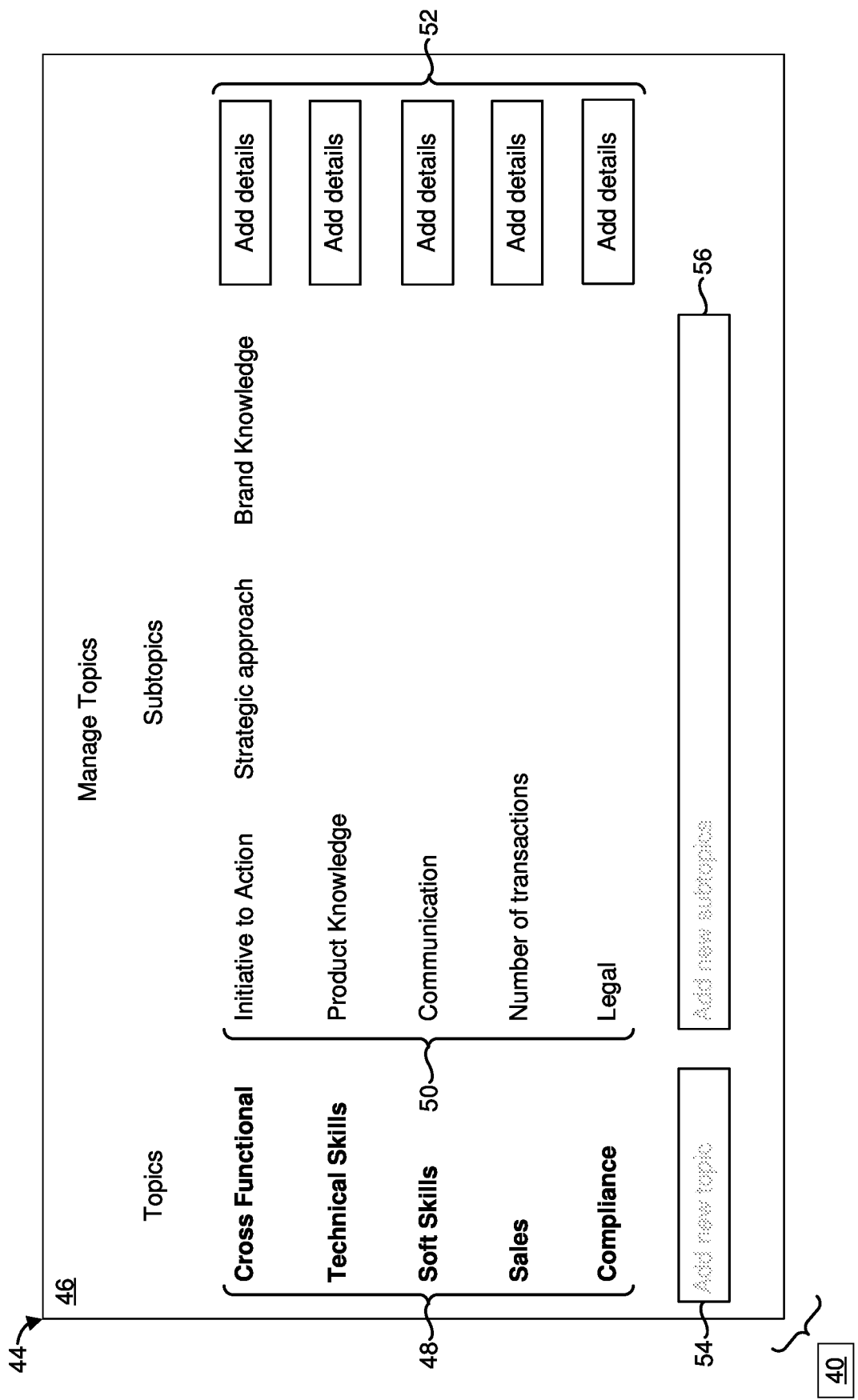

FIG. 1E illustrates an example topic management graphical user interface (GUI) 46 ("topic management interface 46", hereinafter for the sake of brevity) that the administrator device 40 displays on a display 44 of the administrator device 40. In various implementations, the topic management interface 46 allows the administrator 42 to specify topics 48 and/or subtopic 50 that are associated with a physical article and/or a user type. For example, in some implementations, the topic management interface 46 allows the administrator 42 to specify the topics 48 and/or the subtopics 50 that the user 22 (e.g., a medical representative) needs to understand in order to accurately and/or effectively convey information regarding a pharmaceutical article (e.g., a pharmaceutical drug or a medical device) to healthcare providers (e.g., to physicians, nurse practitioners, physician assistants, nurses and/or medical assistants).

In some implementations, the topics 48 correspond to skills that the user 22 needs to acquire and/or improve upon in order to accurately and/or effectively convey information regarding a pharmaceutical article. As such, in some implementations, the topics 48 are referred to as skills or competencies. In the example of FIG. 1E, the topics 48 (e.g., competencies) include 'cross functional skills', 'technical skills', 'soft skills', 'sales skills', and 'compliance skills'. In some implementations, the subtopics 50 correspond to behaviors that the user 22 needs to acquire and/or exhibit in order to accurately and/or effectively convey information regarding the pharmaceutical article. As such, in some implementations, the subtopics 50 are referred to as behaviors. In the example of FIG. 1E, the subtopics 50 (e.g., behaviors) for the 'cross functional' topic include 'initiative to action', 'strategic approach' and 'brand knowledge', the subtopics 50 for the 'technical skills' topic include 'product knowledge', the subtopics 50 for the 'soft skills' topic include 'communication', the subtopics 50 for the 'sales' topic include 'number of transactions' (e.g., number of physical articles sold, for example, a number of pharmaceutical drugs prescribed), and the subtopics 50 for the 'compliance' topic include 'legal.

In some implementations, the topic management interface 46 includes add detail affordances 52 for adding details regarding the topics 48 and/or the subtopics 50. For example, in some implementations, an administrator 42 can add subtopics 50 to a particular topic 48 by pressing a corresponding add details affordance 52. In some implementations, the topic management interface 46 includes a new topic affordance 54 into which the administrator 42 can type a string corresponding to a new topic, and a new subtopic affordance 56 into which the administrator 42 can type a string corresponding to new subtopics related to the new topic.

Figure 1F:
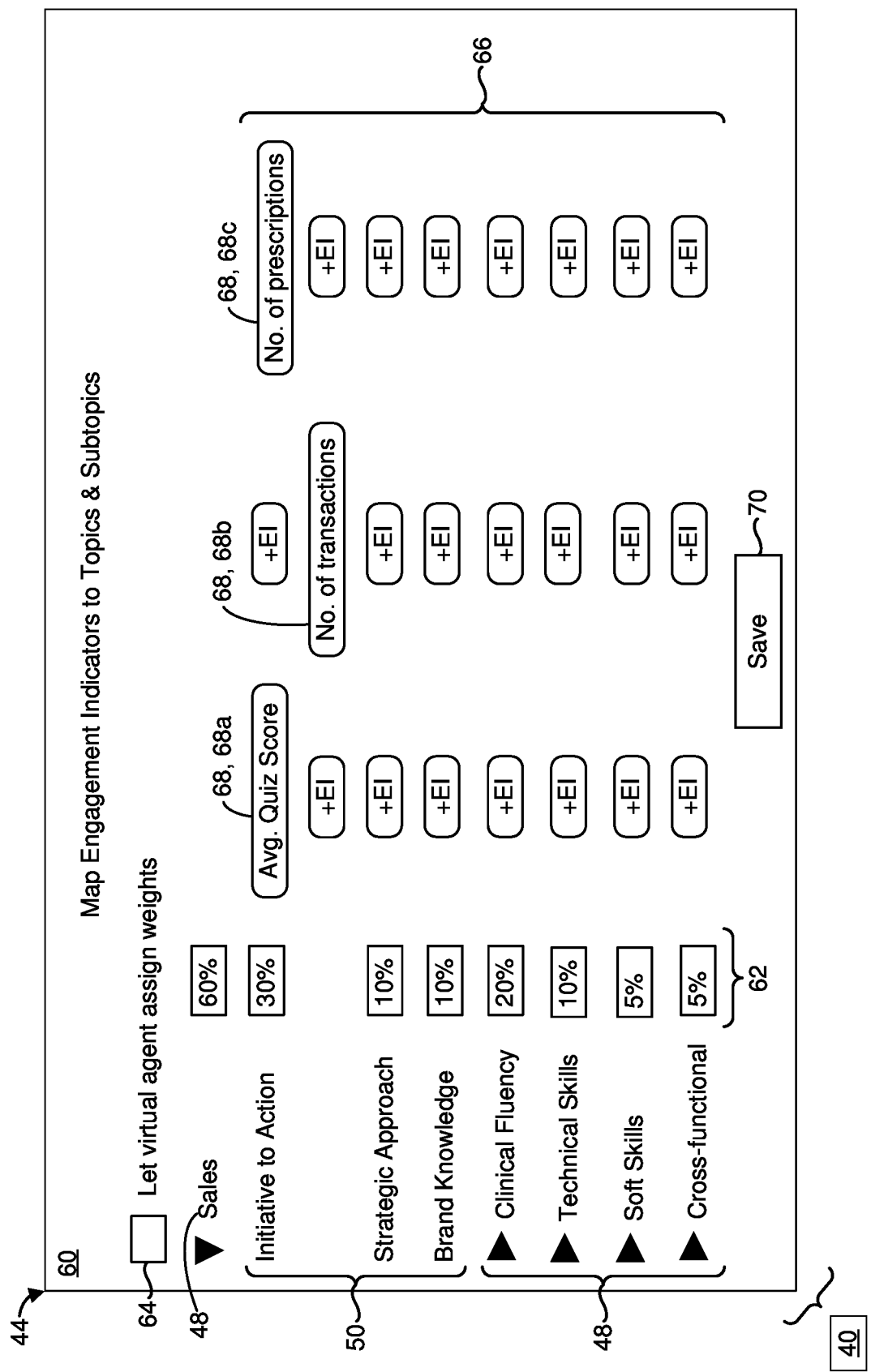

FIG. 1F illustrates a mapping interface 60 that allows the administrator 42 to map engagement indicators 68 to the topics 48 and/or the subtopics 50. In some implementations, the engagement data 250 (shown in FIG. 1A) indicates values (e.g., numerical values) for the engagement indicators 68. In some implementations, the topics 48 and/or the subtopics 50 are associated with corresponding weights 62. In some implementations, the administrator 42 manually assigns the weights 62 to the topics 48 and/or the subtopics 50. Alternatively, in some implementations, a device (e.g., a virtual agent implemented by the device) determines the weights 62. In the example of FIG. 1F, the mapping interface 60 includes an automatic weight assignment option 64 that, when activated, allows a virtual agent to automatically assign the weights 62 without requiring the administrator 42 to manually enter the weights 62.

In some implementations, the mapping interface 60 includes engagement indicator affordances 66 for associating different engagement indicators 68 with the topics 48 and/or the subtopics 50. In some implementations, the administrator 42 activates (e.g., taps, clicks or presses) an engagement indicator affordance 66 to view a list of engagement indicators 68 that can be associated with a particular topic 48 and/or a particular subtopic 50. In the example of FIG. 1F, an average quiz score 68a, a number of transactions 68b (e.g., a number of sales) and a number of prescriptions 68c are associated with the 'initiative to action' subtopic. As such, in the example of FIG. 1F, the engagement monitoring engine 200 determines a comprehension score for the 'initiative to action' subtopic based on a combination of the average quiz score 68a, the number of transactions 68b and the number of prescriptions 68c. The mapping interface 60 includes a save affordance 70 for saving a mapping between the engagement indicators 68, and the topics 48 and/or subtopics 50.

Figure 2:
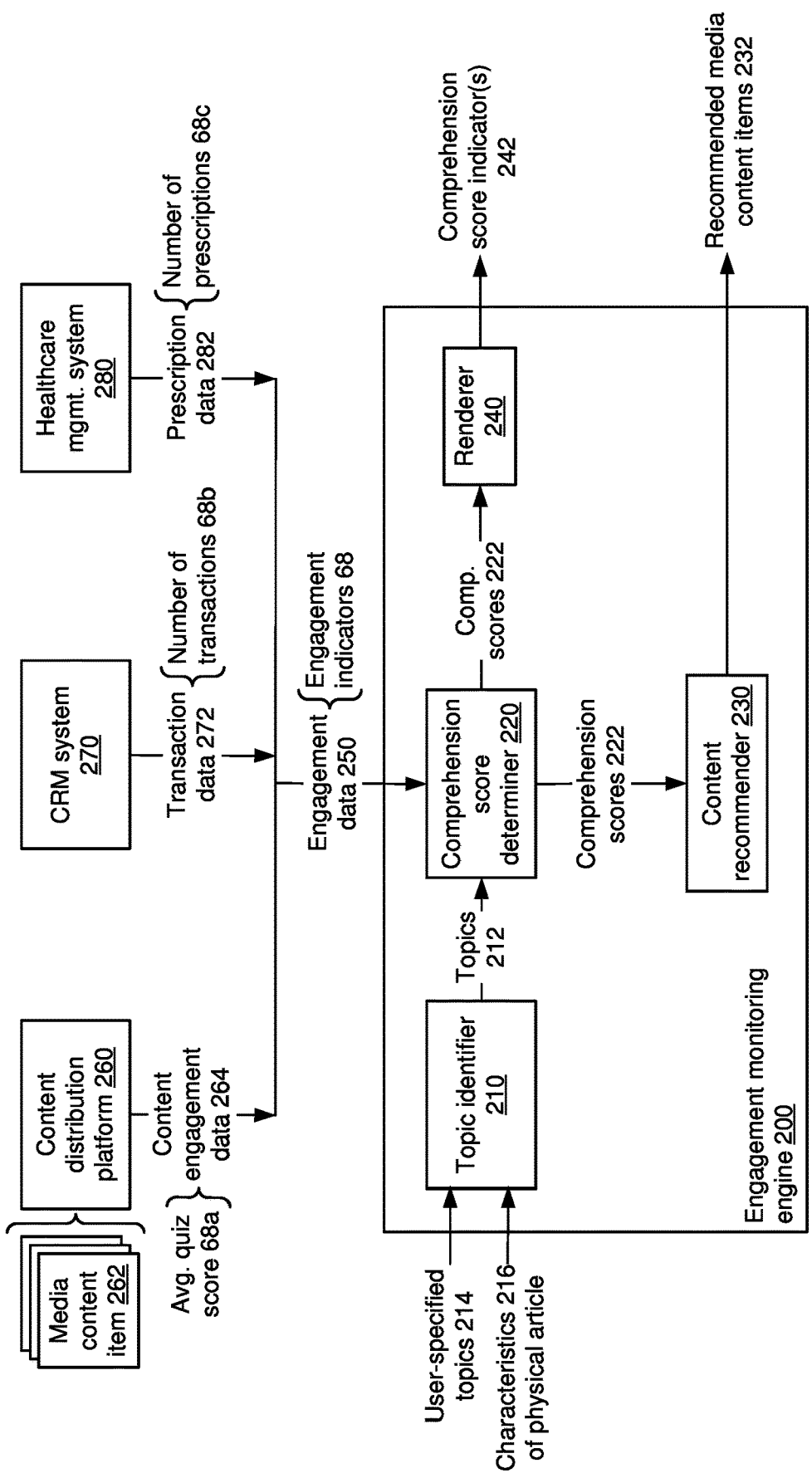
FIG. 2 is a block diagram of an engagement monitoring engine in accordance with some implementations.

FIG. 2 illustrates a block diagram of the engagement monitoring engine 200 in accordance with some implementations. In some implementations, the engagement monitoring engine 200 includes a topic identifier 210, a comprehension score determiner 220, a content recommender 230 and a renderer 240.

In various implementations, the topic identifier 210 identifies a set of one or more topics 212 ("topics 212", hereinafter for the sake of brevity) that are associated with an article (e.g., a physical article, for example, a pharmaceutical article such as a pharmaceutical drug or a medical device)

that the engagement monitoring engine 200 is monitoring. In some implementations, the topic identifier 210 obtains a set of one or more user-specified topics 214 ("user-specified topics 214", hereinafter for the sake of brevity), and the topic identifier 210 identifies the topics 212 based on the user-specified topics 214. For example, in some implementations, the topics 212 are the same as the user-specified topics 214. In some implementations, the topics 212 are a subset of the user-specified topics 214. In some implementations, the topic identifier 210 obtains the user-specified topics 214 from the administrator device 40. For example, in some implementations, the topic identifier 210 receives the user-specified topics 214 via the topic management interface 46 shown in FIG. 1E. In some implementations, the topics 212 include skills or competencies required to accurately and/or effectively convey information regarding a pharmaceutical article. In some implementations, the topics 212 include skills or competencies required to accurately and/or effectively control (e.g., manage) a medical condition that a pharmaceutical article treats.

In some implementations, the topic identifier 210 identifies the topics 212 based on a set of one or more characteristic values 216 ("characteristics 216", hereinafter for the sake of brevity) associated with the physical article. In some implementations, the characteristics 216 indicate a particular type of the physical article (e.g., a pharmaceutical drug or a medical device), and the topics 212 include topics that the administrator 42 associated with that particular type of the physical article. In some implementations, the topic identifier 210 utilizes the characteristics 216 to identify another physical article that is within a similarity threshold of the physical article, and the topics 212 are the same as topics associated with the other physical article. For example, in some implementations, the characteristics 216 indicate that the physical article is a new blood glucose reducing drug, the topic identifier 210 determines the topics 212 for the new blood glucose reducing drug by copying topics of an older blood glucose reducing drug.

In various implementations, the comprehension score determiner 220 determines respective comprehension scores 222 for the topics 212 based on the engagement data 250. As described herein, in some implementations, the comprehension scores 222 indicate how well the user 22 understands the topics 212. In some implementations, the topics 212 correspond to competencies (e.g., skills), and the comprehension scores 222 indicate an ability of the user 22 to apply the competencies. In some implementations, the comprehension scores 222 indicate whether the user 22 is a novice (e.g., a beginner), proficient, advanced, a coach or an expert in a particular topic (e.g., a particular competency). In some implementations, the engagement data 250 includes the engagement indicators 68 shown in FIG. 1F, and the engagement monitoring engine 200 generates the comprehension scores 222 based on one or more of the engagement indicators 68.

In some implementations, the engagement monitoring engine 200 obtains at least a portion of the engagement data 250 from a content distribution platform 260 (e.g., a learning management system (LMS)) that stores various media content items 262. In some implementations, at least a portion of the engagement data 250 includes content engagement data 264 that indicates engagement with a subset of the media content items 262 that relate to the physical article. In some implementations, the content distribution platform 260 stores media content items 262 that provide information regarding various pharmaceutical articles, and the content engagement data 264 indicates engagement with a subset of the media content items 262 that provide information regarding a particular one of the pharmaceutical articles.

In some implementations, the content engagement data 264 indicates whether or not the user 22 has engaged with (e.g., viewed) a subset of the media content items 262 that relate to a particular physical article (e.g., a particular pharmaceutical article). In some implementations, the content engagement data 264 indicates a percentage of the media content items that the user 22 has viewed in the subset of media content items 262 that related to a particular physical article. In some implementations, the content engagement data 264 indicates a number of times that the user 22 has viewed a media content item 262 related to a particular physical article. In some implementations, at least one of the media content items 262 include a quiz (e.g., a test), and the content engagement data 264 includes a quiz score (e.g., a test score) on the quiz. For example, in some implementations, the content engagement data 264 indicates the average quiz score 68a shown in FIG. 1F.

In some implementations, the engagement monitoring engine 200 obtains at least a portion of the engagement data 250 from a client relations management (CRM) system 270. In some implementations, at least a portion of the engagement data 250 includes transaction data 272 that the engagement monitoring engine 200 obtains from the CRM system 270. In some implementations, the transaction data 272 includes event data that indicates a number of times that the user 22 has met with authorized recommenders of the physical article. For example, in some implementations, the transaction data 272 indicates a number of times that a medical representative has met with licensed healthcare providers that are authorized to prescribe a pharmaceutical drug or a medical device. In some implementations, the transaction data 272 indicates a number of units of the physical article that have been sold by a manufacturer of the physical article. For example, the transaction data 272 indicates a number of packages of a pharmaceutical drug or a number of units of a medical device that have been sold. In some implementations, the transaction data 272 indicates the number of transactions 68b (shown in FIG. 1F) related to the physical article.

In some implementations, the engagement monitoring engine 200 obtains at least a portion of the engagement data 250 from a healthcare management system 280 that stores prescription data 282. In some implementations, the prescription data 282 includes prescriptions that have been generated by healthcare providers for patients. In some implementations, the prescription data 282 is anonymized in order to remove any private information related to the patients (e.g., in order to comply with privacy laws and regulations related to medical data, for example, in order to comply with the Health Insurance Portability and Accountability Act (HIPAA)). In some implementations, the prescription data 282 indicates a number of prescriptions that have been generated for a particular pharmaceutical article in a geographical region associated with (e.g., assigned to) the user 22, and a number of prescriptions that have been generated for another pharmaceutical article (e.g., a comparable pharmaceutical article that is manufactured by another manufacturer) in the same geographical region. For example, in some implementations, the prescription data 282 indicates the number of prescriptions 68c shown in FIG. 1F. In various implementations, the healthcare management system 280 is replaced by a recommendation management system that tracks recommendations of a physical article by authorized recommenders, and the prescription data 282 is replaced by recommendation data that indicates a number of recommendations that authorized recommenders made for the physical article in a geographical region associated with the user 22.

In some implementations, the comprehension score determiner 220 utilizes different mathematical functions to generate the comprehension scores 222. For example, in some implementations, the comprehension score determiner 220 utilizes a first mathematical function to generate a first one of the comprehension scores 222 for a corresponding first one of the topics 212, a second mathematical function to generate a second one of the comprehension scores 222 for a corresponding second one of the topics 212, . . . , and an nth mathematical function to generate an nth one of the comprehension scores 222 for a corresponding nth one of the topics 212. In some implementations, different mathematical functions assign different weights to the engagement indicators 68. In other words, different mathematical functions utilize different coefficient values for the engagement indicators 68. For example, the first mathematical function may assign a higher coefficient value to the average quiz score 68*a* than the second mathematical function thereby assigning more weight to the average quiz score 68*a* in determining the first one of the comprehension scores 222. As another example, the first mathematical function may assign a lower coefficient value to the number of prescriptions 68*c* than the second mathematical function thereby assigning less weight to the number of prescriptions 68*c* in determining the first one of the comprehension scores 222.

In some implementations, the comprehension score determiner 220 includes a neural network system (e.g., a set of one or more neural networks) that receive the engagement data 250 as an input, and generate the comprehension scores 222 for the topics 212 as an output. In some implementations, the neural network system accepts the content engagement data 264, the transaction data 272 and the prescription data 282 as inputs, and generates the comprehension scores 222 for the topics 212 as outputs.

In some implementations, the content recommender 230 implements a content recommendation engine that recommends, based on the comprehension scores 222, a subset of the media content items 262 available through the content distribution platform 260. In some implementations, the subset of the media content items 262 recommended by the content recommender 230 based on the comprehension scores 222 is referred to as the recommended media content items 232. As shown in FIG. 1A, in some implementations, the content recommender 230 transmits the recommended media content items 232 or an indication of (e.g., identifiers of) the recommended media content items 232 to the user device 20.

In some implementations, the recommended media content items 232 provide information regarding the topics 212 with comprehension scores 222 that are lower than a threshold comprehension score. In some implementations, the recommended media content items 232 do not include media content items that provide information regarding the topics 212 with comprehension scores 222 that are greater than the threshold comprehension score. As such, the recommended media content items 232 allow the user to increase his/her comprehension level in the topics 212 with relatively low comprehension scores 222.

In some implementations, the recommended media content items 232 include more media content items that provide information regarding the topics 212 with weights that are greater than a threshold weight, and fewer media content items that provide information regarding the topics 212 with weights that are less than the threshold weight. For example, in some implementations, the recommended media content items 232 include a first number of recommended media content items that provide information regarding a first one of the topics 212 with a first weight and a second number of recommended media content items that provide information regarding a second one of the topics 212 with a second weight that is different from the first weight. In such implementations, the first number of recommended media content items is greater than the second number of recommended media content items in response to the first weight being greater than the second weight. As such, the recommended media content items 232 allow the user 22 to view more information regarding topics 212 that are associated with a relatively high weight, and less information regarding topics 212 that are associated with a relatively low weight.

In some implementations, the renderer 240 causes the comprehension score indicators 242 indicative of the comprehension scores 222 to be displayed on a display. For example, in some implementations, the renderer 240 triggers the administrator device 40 to display the comprehension score indicators 242 on the display 44 of the administrator device 40. In some implementations, the renderer 240 triggers the user device 20 to display the comprehension score indicators 242 on the display 24 of the user device 20.

Figure 3:
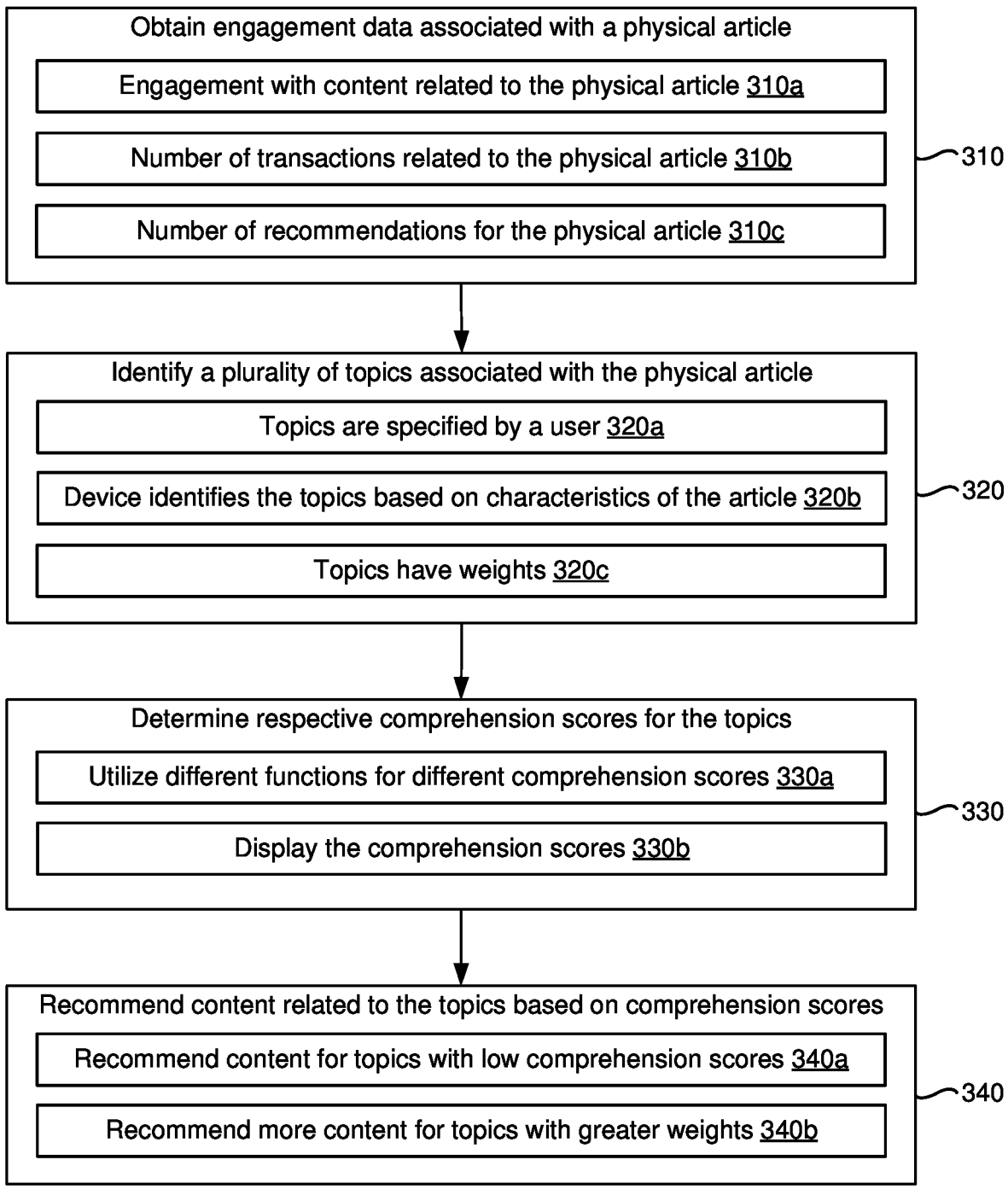
FIG. 3 is a flowchart representation of a method of monitoring engagement in accordance with some implementations.

FIG. 3 is a flowchart representation of a method 300 of monitoring engagement in accordance with some implementations. In various implementations, the method 300 is performed by a device including a non-transitory memory and a processor coupled with the non-transitory memory (e.g., the engagement monitoring engine 200 shown in FIGS. 1A and 2, the user device 20 shown in FIGS. 1A-1D and/or the administrator device 40 shown in FIGS. 1A and 1E-1F). In some implementations, the method 300 is performed by processing logic, including hardware, firmware, software, or a combination thereof. In some implementations, the method 300 is performed by a processor executing code stored in a non-transitory computer-readable medium (e.g., a memory). In some implementations, the method 300 is performed at a server or a cloud computing platform.

As represented by block 310, in some implementations, the method 300 includes obtaining engagement data indicating engagement associated with a pharmaceutical article. For example, as shown in FIGS. 1A and 2, the engagement monitoring engine 200 obtains the engagement data 250 indicating engagement associated with a physical article. In some implementations, the physical article includes a pharmaceutical article. In some implementations, the pharmaceutical article includes a pharmaceutical drug. In some implementations, the pharmaceutical article includes a medical device. In some implementations, obtaining the engagement data includes receiving the engagement data from another device (e.g., from a remote data source). In some implementations, obtaining the engagement data includes detecting the engagement data via one or more sensors.

As represented by block 310*a*, in some implementations, the engagement data indicates engagement with a media content item (e.g., a pharmaceutical content item) related to the pharmaceutical article. For example, as shown in FIG. 2, in some implementations, the engagement data 250 includes the content engagement data 264. In some implementations, the engagement data indicates whether or not a user has viewed the media content item. In some implementations, the engagement data indicates whether or not the user has completed a course providing information regarding the pharmaceutical article. In some implementations, the engagement data indicates a quiz score on a quiz related to the pharmaceutical article. For example, as shown in FIG. 2, in some implementations, the content engagement data 264 includes the average quiz score 68a.

As represented by block 310b, in some implementations, the engagement data indicates a number of transactions related to the pharmaceutical article. For example, as shown in FIG. 2, in some implementations, the engagement data 250 includes the transaction data 272. In some implementations, the engagement data indicates a quantity of the pharmaceutical article that has been transferred from a manufacturer of the pharmaceutical article, for example, a quantity of the pharmaceutical article that has been sold by the manufacturer. For example, as shown in FIG. 2, in some implementations, the transaction data 272 indicates the number of transactions 68b.

As represented by block 310c, in some implementations, the engagement data indicates a number of recommendations for the pharmaceutical article by authorized recommenders. In some implementations, the physical article is a pharmaceutical drug and the engagement data indicates a number of times that the pharmaceutical drug has been prescribed over a period of time by healthcare providers in a particular geographical region. For example, as shown in FIG. 2, in some implementations, the engagement data 250 includes prescription data 282 that indicates a number of prescriptions 68c.

As represented by block 320, in some implementations, the method 300 includes identifying a plurality of topics (e.g., a plurality of pharmaceutical topics, for example, medical conditions that the pharmaceutical article is used to treat, dosages, method of administration, side effects, etc.) associated with the pharmaceutical article. For example, as shown in FIG. 2, the topic identifier 210 identifies the topics 212 associated with the physical article. In some implementations, the topics associated with the pharmaceutical article include topics that a user needs to understand in order to accurately and/or effectively convey information regarding the pharmaceutical article. In some implementations, the topics associated with the pharmaceutical article include competencies (e.g., skills) that the user needs to have in order to increase the engagement associated with the pharmaceutical article (e.g., to increase usage of the pharmaceutical article, for example, to increase the number of prescriptions written for a particular pharmaceutical article).

As represented by block 320a, in some implementations, identifying the plurality of topics comprises detecting a user input that associates the plurality of topics with the pharmaceutical article. For example, as shown in FIG. 1E, in some implementations, the administrator device 40 provides the topics via the topic management interface 46. As shown in FIG. 2, in some implementations, the topic identifier 210 identifies the topics 212 based on the user-specified topics 214. For example, in some implementations, the topics 212 are the same as or within a similarity threshold of the user-specified topics 214.

As represented by block 320b, in some implementations, identifying the plurality of topics comprises determining the plurality of topics based on a set of characteristic values associated with the pharmaceutical article. For example, as shown in FIG. 2, in some implementations, the topic identifier 210 identifies the topics 212 based on the characteristics 216 of the physical article. For example, in some implementations, identifying the plurality of topics comprises determining the plurality of topics based on a second plurality of topics associated with a second pharmaceutical article that is within a similarity threshold of the pharmaceutical article. In some implementations, a composition of the second pharmaceutical article is the same as a composition of the pharmaceutical article. For example, in some implementations, the pharmaceutical article and the second pharmaceutical article are pharmaceutical drugs with the same chemical ingredients.

As represented by block 320c, in some implementations, the plurality of topics is associated with respective weights that indicate corresponding degrees of association with the physical article. For example, as shown in FIG. 1F, the topics 48 and/or the subtopics 50 are associated with the weights 62. In some implementations, the method 300 includes detecting a user input that specifies the respective weights for the plurality of topics. For example, as shown in FIG. 1F, in some implementations, the administrator device 40 allows the administrator to specify the weights 62 via the mapping interface 60. In some implementations, a virtual agent automatically determines the respective weights for the plurality of topics based on a set of one or more characteristic values associated with the physical article. For example, as shown in FIG. 1F, in some implementations, the mapping interface 60 provides the automatic weight assignment option 64 to allow a virtual agent to automatically determine the weights 62.

As represented by block 330, in some implementations, the method 300 includes determining respective comprehension scores for the plurality of topics based on the engagement data. For example, as shown in FIG. 2, the comprehension score determiner 220 determines the comprehension scores 222 for the topics 212 based on the engagement data 250 (e.g., based on the engagement indicators 68 indicated by the engagement data 250).

As represented by block 330a, in some implementations, determining the respective comprehension scores comprises determining a first one of the respective comprehension scores based on a first function of an amount of engagement indicated by the engagement data, and determining a second one of the respective comprehension scores based on a second function of the amount of engagement indicated by the engagement data. In some implementations, the second function is different from the first function. For example, in some implementations, the device determines a first score for clinical fluency in a pharmaceutical article based on a first function of a quiz score on a quiz related to the pharmaceutical article, a number of transactions related to the pharmaceutical article and a number of prescriptions for the pharmaceutical article. In some implementations, the device determines a second score for technical knowledge of the pharmaceutical article based on a second function of the quiz score, the number of transactions related to the pharmaceutical article and the number of prescriptions for the pharmaceutical article.

In some implementations, the respective comprehension scores are proportional to an amount of engagement indicated by the engagement data. In some implementations, a first one of the respective comprehension scores is directly proportional to an amount of engagement indicated by the engagement data and a second one of the respective comprehension scores is inversely proportional to the amount of engagement indicated by the engagement data.

As represented by block 330b, in some implementations, the device further comprises a display, and the method further comprises displaying the respective comprehension scores for the plurality of topics on the display. For example, as shown in FIG. 2, the renderer 240 causes the comprehension score indicators 242 to be rendered on a display. As another example, as shown in FIG. 1A, in some implementations, the administrator device 40 displays the comprehension score indicators 242 on the display 44 of the administrator device 40. In some implementations, the method 300 includes highlighting a subset of the respective comprehension scores that are below a threshold score. For example, in some implementations, the device displays comprehension scores that are below the threshold score with a first visual property (e.g., a first font, a first color, a first text size, etc.), and the comprehension scores that are greater than the threshold score with a second visual property (e.g., a second font, a second color, a second text size, etc.) that is different from the first visual property.

In some implementations, determining the respective comprehension scores for the plurality of topics provides a more granular view of how well a user of a device (e.g., the user 22 shown in FIG. 1A) understands individual topics related to the physical article, for example, as opposed to how well the user understands the physical article as a whole. Obtaining a more granular view of how well the user understands the individual topics allows the device to recommend and/or present content (e.g., the recommended media content items 232 shown in FIGS. 1A and 2) that may help the user in increasing the user's understanding of the individual topics and consequently increase engagement with the physical article.

As represented by block 340, in some implementations, the method 300 includes recommending a set of one or more media content items (e.g., a set of one or more pharmaceutical content items) related to a subset of the plurality of topics based on the respective comprehension scores for the plurality of topics. For example, as shown in FIG. 2, the content recommender 230 recommends the recommended media content items 232 based on the comprehension scores 222. In some implementations, the method 300 includes transmitting the recommended set of media content items to a device. For example, as shown in FIG. 1A, the engagement monitoring engine 200 provides the recommended media content items 232 or an indication thereof (e.g., identifiers identifying the recommended media content items 232) to the user device 20. In some implementations, the method 300 includes triggering representations of the recommended media content items to be displayed on a display. For example, as shown in FIG. 1B, the user device 20 displays the representations 26 of the recommended media content items 232.

As represented by block 340a, in some implementations, recommending the set of one or more media content items comprises recommending a first media content item related to a first one of the plurality of topics in response to a corresponding first one of the respective comprehension scores being less than a threshold score, and forgo recommending a second media content item related to a second one of the plurality of topics in response to a corresponding second one of the respective comprehension scores being greater than the threshold score. In some implementations, recommending media content items for topics that the user does not understand as well as desired tends to increase an overall understanding of the physical article by the user.

As represented by block 340b, in some implementations, recommending the set of one or more media content items comprises in response to a first one of the respective comprehension scores of a first one of the plurality of topics being less than a threshold score, recommending a first number of media content items related to the first one of the plurality of topics. In some implementations, the first number is based on a first weight of the first one of the plurality of topics. In some implementations, the method 300 includes in response to a second one of the respective comprehension scores of a second one of the plurality of topics being less than the threshold score, recommending a second number of media content items related to the second one of the plurality of topics. In some implementations, the second number is based on a second weight of the second one of the plurality of topics. In some implementations, the first number of media content items is greater than the second number of media content items in response to the first weight being greater than the second weight even if the first one of the respective comprehension scores and the second one of the respective comprehension scores are the same.

In some implementations, recommending media content items based on the comprehension scores enhances discoverability of content by allowing the device to recommend media content items that a user may not otherwise discover. In some implementations, recommending media content items based on the comprehension scores tends to enhance operability of the device by reducing a need for a user to manually search for media content items that provide information regarding topics that the user does not understand as well as desired. In some implementations, recommending media content items based on comprehension scores tends to trigger an increase in the comprehension scores over a period of time. In some implementations, recommending media content items for topics that the user does not understand as well as desired tends to increase an overall understanding of the physical article by the user.

In some implementations, the method 300 includes recommending to an administrator device to create a new media content item that provides information regarding a particular topic in response to determining that a corresponding comprehension score for the particular topic is lower than a threshold comprehension score, and that existing media content items that provide information regarding the particular topic are not effective at increasing the corresponding comprehension score for the particular topic. In some implementations, determining that the existing media content items are ineffective includes determining that a user has reviewed the existing media content items multiple times and the comprehension score for the particular topic has not increased beyond the threshold comprehension score.

Figure 4:
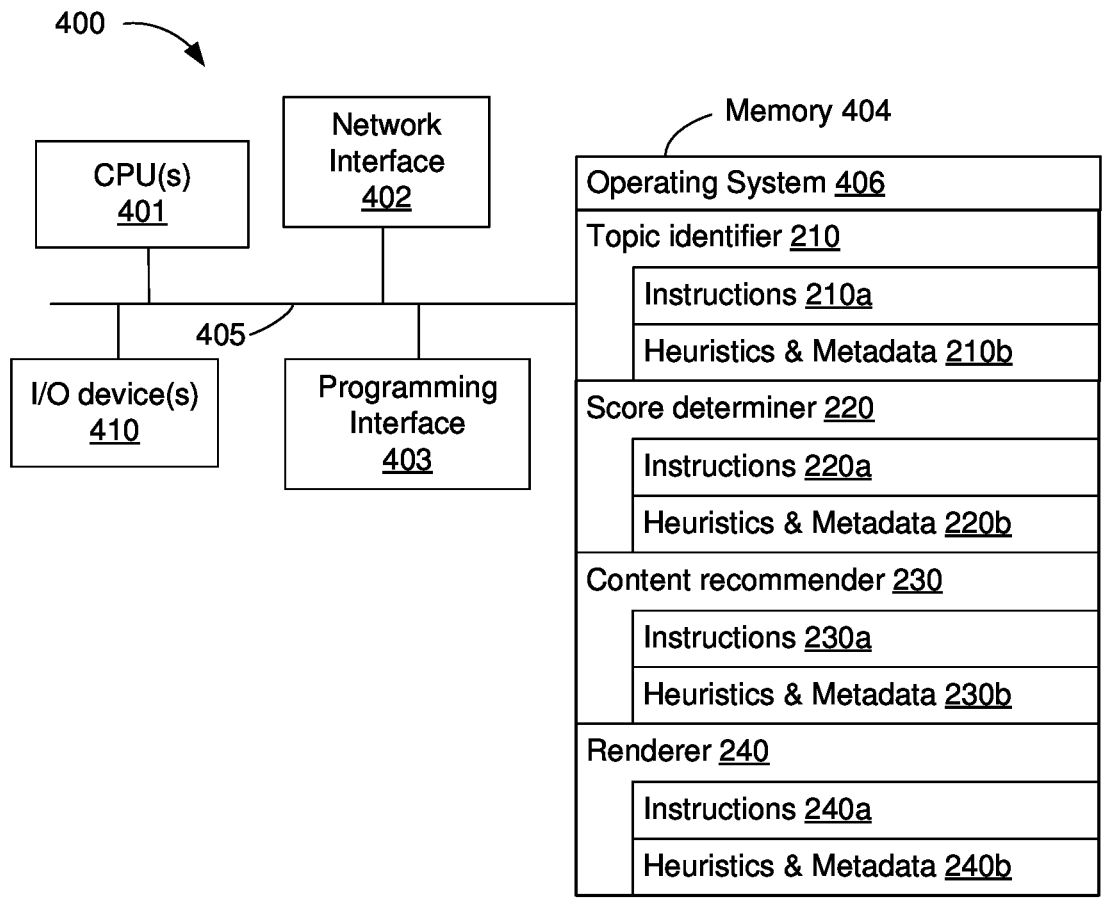
FIG. 4 is a block diagram of a device that monitors engagement in accordance with some implementations.

FIG. 4 is a block diagram of a device 400 that monitors engagement associated with a physical article in accordance with some implementations. In some implementations, the device 400 implements the engagement monitoring engine 200 shown in FIGS. 1A and 2, the user device 20 shown in FIGS. 1A-1D, and/or the administrator device 40 shown in FIGS. 1A, 1E and 1F. In some implementations, the device 400 is implemented by a server. In some implementations, the device 400 is implemented by a cloud computing platform. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations, the device 400 includes one or more processing units (CPUs) 401, a network interface 402, a programming interface 403, a memory 404, one or more input/output (I/O) devices 410, and one or more communication buses 405 for interconnecting these and various other components.

In some implementations, the network interface 402 is provided to, among other uses, establish and maintain a metadata tunnel between a cloud hosted network management system and at least one private network including one or more compliant devices. In some implementations, the one or more communication buses 405 include circuitry that interconnects and controls communications between system components. The memory 404 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 404 optionally includes one or more storage devices remotely located from the one or more CPUs 401. The memory 404 comprises a non-transitory computer readable storage medium.

In some implementations, the memory 404 or the non-transitory computer readable storage medium of the memory 404 stores the following programs, modules and data structures, or a subset thereof including an optional operating system 406, the topic identifier 210, the comprehension score determiner 220, the content recommender 230 and the renderer 240. In various implementations, the device 400 performs the method 300 shown in FIG. 3. In some implementations, the topic identifier 210 includes instructions 210a, and heuristics and metadata 210b for identifying topics associated with a physical article. In some implementations, the comprehension score determiner 220 includes instructions 220a, and heuristics and metadata 220b for determining comprehension scores for the topic identified by the topic identifier 210. In some implementations, the content recommender 230 includes instructions 230a, and heuristics and metadata 230b for recommending media content items based on the comprehension scores. In some implementations, the renderer 240 includes instructions 240a, and heuristics and metadata 240b for causing representations of the comprehension scores and/or representations of the recommended media content items to be rendered (e.g., displayed) on a display.

In various implementations, the one or more I/O devices 410 include one or more sensors for detecting engagement data associated with a physical article (e.g., the engagement data 250 shown in FIGS. 1A and 2). In some implementations, the one or more I/O devices 410 include a receiver for obtaining engagement data associated with a physical article. In some implementations, the one or more I/O devices 410 include a transmitter for transmitting the comprehension scores and/or the recommended media content items. In some implementations, the one or more I/O devices 410 include a display for displaying a GUI (e.g., the GUI 25 shown in FIGS. 1B-1D, the topic management interface 46 shown in FIG. 1E and/or the mapping interface 60 shown in FIG. 1F). In some implementations, the one or more I/O devices 410 include a speaker for outputting audible signals corresponding to the recommended media content items. In some implementations, the one or more I/O devices 410 include a haptic device (e.g., a vibration device, for example, a motor with an unbalanced load or a piezoelectric device) for outputting haptic responses corresponding to the recommended media content items.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first", "second", etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting", that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
at a device including a non-transitory memory, a display and a processor coupled with the non-transitory memory and the display:
receiving a plurality of recommended media content items that provide information regarding a subset of a plurality of topics related to a pharmaceutical article, wherein a content recommendation engine identifies the plurality of recommended media content items based on respective comprehension scores of a medical representative for the subset of the plurality of topics being below a threshold comprehension score;
displaying, on the display, a graphical user interface (GUI) that includes a first selectable tile that represents a first recommended media content item from the plurality of recommended media content items recommended by the content recommendation engine and a second selectable tile that represents a second recommended media content item from the plurality of recommended content items recommended by the content recommendation engine;

detecting a tap gesture selecting the first selectable tile that represents the first recommended media content item; and in response to detecting the tap gesture selecting the first selectable tile that represents the first recommended media content item, displaying, within the GUI, an expanded view of the first selectable tile that includes:

a video, a play button for playing the video, and a progress bar with a filled portion that corresponds to a current comprehension score indicating how well the medical representative understands a first topic covered by the first recommended media content item and a visual marker in an unfilled portion of the progress bar indicating a target comprehension score that the medical representative is expected to have upon viewing the video.

2. The method of claim 1, wherein the expanded view of the first selectable tile further displays a numerical value adjacent to the progress bar, wherein the numerical value is a difference between the current comprehension score and the target comprehension score.

3. The method of claim 1, wherein the expanded view of the first selectable tile further displays a text string adjacent to the progress bar, wherein the text string describes a comprehension level of the medical representative with respect to the first topic and the text string is generated based on a mapping of comprehension scores to comprehension levels.

4. The method of claim 1, wherein the expanded view of the first selectable tile further includes:

a second progress bar that is displayed below the progress bar, wherein the second progress bar includes:

a filled portion that corresponds to a second current comprehension score indicating how well the medical representative understands a second topic covered by the first recommended media content item, and a second visual marker in an unfilled portion of the second progress bar indicating a second target comprehension score that the medical representative is expected to have upon viewing the video.

5. The method of claim 4, wherein the expanded view of the first selectable tile further includes:

a third progress bar that is displayed below the second progress bar, wherein the third progress bar includes:

a filled portion that corresponds to a third current comprehension score indicating how well the medical representative understands a third topic covered by the first recommended media content item, and a third visual marker in an unfilled portion of the third progress bar indicating a third target comprehension score that the medical representative is expected to have upon viewing the video.

6. The method of claim 5, wherein the first selectable tile includes a first symbol of the first topic, a second symbol of the second topic and a third symbol of the third topic in order to indicate that the first recommended media content item provides information regarding the first topic, the second topic and the third topic.

7. The method of claim 1, wherein the first selectable tile includes a first symbol of the first topic covered by the first recommended media content item, a second symbol of a second topic covered by the first recommended media content item and a third symbol of a third topic covered by the first recommended media content item; and wherein the second selectable tile includes a fourth symbol of a fourth topic covered by the second recommended media content item and a fifth symbol of a fifth topic covered by the second recommended media content item.

8. The method of claim 1, wherein the first selectable tile and the second selectable tile are displayed in a vertical configuration such that the first selectable tile is closer to a top edge of the device than the second selectable tile.

9. A non-transitory memory storing one or more programs, which, when executed by one or more processors of a device with a display, cause the device to:

receive a plurality of recommended media content items that provide information regarding a subset of a plurality of topics related to a pharmaceutical article, wherein a content recommendation engine identifies the plurality of recommended media content items based on respective comprehension scores of a medical representative for the subset of the plurality of topics being below a threshold comprehension score;

display, on the display, a graphical user interface (GUI) that includes a first selectable tile that represents a first recommended media content item from the plurality of recommended media content items recommended by the content recommendation engine and a second selectable tile that represents a second recommended media content item from the plurality of recommended content items recommended by the content recommendation engine;

detect a tap gesture selecting the first selectable tile that represents the first recommended media content item; and in response to detecting the tap gesture selecting the first selectable tile that represents the first recommended media content item, display, within the GUI, an expanded view of the first selectable tile GUI element that includes:

a video, a play button for playing the video, and a progress bar with a filled portion that corresponds to a current comprehension score indicating how well the medical representative understands a first topic covered by the first recommended media content item and a visual marker in an unfilled portion of the progress bar indicating a target comprehension score that the medical representative is expected to have upon viewing the video.

10. The non-transitory memory of claim 9, wherein the expanded view of the first selectable tile further displays a numerical value adjacent to the progress bar, wherein the numerical value is a difference between the current comprehension score and the target comprehension score.

11. The non-transitory memory of claim 9, wherein the expanded view of the first selectable tile further displays a text string adjacent to the progress bar, wherein the text string describes a comprehension level of the medical representative with respect to the first topic and the text string is generated based on a mapping of comprehension scores to comprehension levels.

12. The non-transitory memory of claim 9, wherein the expanded view of the first selectable tile further includes:

a second progress bar that is displayed below the progress bar, wherein the second progress bar includes:

a filled portion that corresponds to a second current comprehension score indicating how well the medical representative understands a second topic covered by the first recommended media content item, and a second visual marker in an unfilled portion of the second progress bar indicating a second target comprehension score that the medical representative is expected to have upon viewing the video.

13. The non-transitory memory of claim 12, wherein the expanded view of the first selectable tile further includes:

a third progress bar that is displayed below the second progress bar, wherein the third progress bar includes:

a filled portion that corresponds to a third current comprehension score indicating how well the medical representative understands a third topic covered by the first recommended media content item, and a third visual marker in an unfilled portion of the third progress bar indicating a third target comprehension score that the medical representative is expected to have upon viewing the video.

14. The non-transitory memory of claim 13, wherein the first selectable tile includes a first symbol of the first topic, a second symbol of the second topic and a third symbol of the third topic in order to indicate that the first recommended media content item provides information regarding the first topic, the second topic and the third topic.

15. The non-transitory memory of claim 9, wherein the first selectable tile includes a first symbol of the first topic covered by the first recommended media content item, a second symbol of a second topic covered by the first recommended media content item and a third symbol of a third topic covered by the first recommended media content item; and wherein the second selectable tile includes a fourth symbol of a fourth topic covered by the second recommended media content item and a fifth symbol of a fifth topic covered by the second recommended media content item.

16. The non-transitory memory of claim 9, wherein the first selectable tile and the second selectable tile are displayed in a vertical configuration such that the first selectable tile is closer to a top edge of the device than the second selectable tile.

17. A device comprising:

one or more processors;

a non-transitory memory;

a display; and one or more programs stored in the non-transitory memory, which, when executed by the one or more processors, cause the device to:

receive a plurality of recommended media content items that provide information regarding a subset of a plurality of topics related to a pharmaceutical article, wherein a content recommendation engine identifies the plurality of recommended media content items based on respective comprehension scores of a medical representative for the subset of the plurality of topics being below a threshold comprehension score;

display, on the display, a graphical user interface (GUI) that includes a first selectable tile that represents a first recommended media content item from the plurality of recommended media content items recommended by the content recommendation engine and a second selectable tile that represents a second recommended media content item from the plurality of recommended content items recommended by the content recommendation engine;

detect a tap gesture selecting the first selectable tile that represents the first recommended media content item; and in response to detecting the tap gesture selecting the first selectable tile that represents the first recommended media content item, display, within the GUI, an expanded view of the first selectable tile that includes:

a video, a play button for playing the video, and a progress bar with a filled portion that corresponds to a current comprehension score indicating how well the medical representative understands a first topic covered by the first recommended media content item and a visual marker in an unfilled portion of the progress bar indicating a target comprehension score that the medical representative is expected to have upon viewing the video.

18. The device of claim 17, wherein the expanded view of the first selectable tile further displays a numerical value adjacent to the progress bar, wherein the numerical value is a difference between the current comprehension score and the target comprehension score.

19. The device of claim 17, wherein the expanded view of the first selectable tile further displays a text string adjacent to the progress bar, wherein the text string describes a comprehension level of the medical representative with respect to the first topic and the text string is generated based on a mapping of comprehension scores to comprehension levels.

20. The device of claim 17, wherein the expanded view of the first selectable tile further includes:

a second progress bar that is displayed below the progress bar, wherein the second progress bar includes:

a filled portion that corresponds to a second current comprehension score indicating how well the medical representative understands a second topic covered by the first recommended media content item, and a second visual marker in an unfilled portion of the second progress bar indicating a second target comprehension score that the medical representative is expected to have upon viewing the video.

21. The device of claim 20, wherein the expanded view of the first selectable tile further includes:

a third progress bar that is displayed below the second progress bar, wherein the third progress bar includes:

a filled portion that corresponds to a third current comprehension score indicating how well the medical representative understands a third topic covered by the first recommended media content item, and a third visual marker in an unfilled portion of the third progress bar indicating a third target comprehension score that the medical representative is expected to have upon viewing the video.

22. The device of claim 21, wherein the first selectable tile includes a first symbol of the first topic, a second symbol of the second topic and a third symbol of the third topic in order to indicate that the first recommended media content item provides information regarding the first topic, the second topic and third topic.

* * * * *